United States Patent

King et al.

Patent Number: 4,871,744
Date of Patent: Oct. 3, 1989

[54] CERTAIN 2,3-DIHYDRO-INDOLE-1-CARBOXAMIDO-N-[8-AZABICYCLO(3.2.1)OCTAN-3-YL]DERIVATIVES HAVING 5-HT-ANTAGONIST ACTIVITY

[75] Inventors: Francis D. King; Karen A. Joiner, both of Harlow, England

[73] Assignee: Beecham Group p.l.c., Brentford, England

[21] Appl. No.: 202,224

[22] Filed: Jun. 3, 1988

[30] Foreign Application Priority Data

Mar. 23, 1988 [GB] United Kingdom ............ 8806990

[51] Int. Cl.$^4$ .......... C07D 451/12; C07D 451/14; A61K 31/395
[52] U.S. Cl. .......................... 514/299; 514/304; 548/372; 546/112; 546/126
[58] Field of Search ............ 546/112, 126; 514/299, 514/304

[56] References Cited

FOREIGN PATENT DOCUMENTS

| | | | |
|---|---|---|---|
| 0115933A2 | 8/1984 | European Pat. Off. | 546/112 |
| 0158265A2 | 10/1985 | European Pat. Off. | 546/112 |
| 0200444A2 | 5/1986 | European Pat. Off. | 546/126 |
| 201165A2 | 11/1986 | European Pat. Off. | 546/126 |
| 8400166 | 1/1984 | PCT Int'l Appl. | 546/126 |
| 8501048 | 3/1985 | PCT Int'l Appl. | 546/126 |
| 2100259A | 12/1982 | United Kingdom | 546/127 |
| 2125398A | 3/1984 | United Kingdom | 546/127 |

OTHER PUBLICATIONS

J. L. G. Nilsson et al., "Some Quinuclidine Derivatives with Potential Antimalarial Activity", Acta Pharm. Suecica, 5, pp. 71–76 (1968) [Nilsson et al.].
"Serotonin Antagonists—Too Much Hype?", SCRIP, No. 1215, p. 26 (Jun. 19, 1987) [SCRIP I].
"Glaxo's GR-38032F in Emesis CT Results", SCRIP, No. 1219, p. 24 (Jul. 3, 1987) [SCRIP II].
J. Lars et al., "Some Quinuclidine Derivatives with Potential Antimalarial Activity", Acta Pharm. Suecica, 5, pp. 71–76 (1968).

Primary Examiner—Alan L. Rotman
Attorney, Agent, or Firm—James F. Haley, Jr.; David K. Barr; Emily A. Evans

[57] ABSTRACT

Compounds of formula (I) and pharmaceutically acceptable salts thereof;

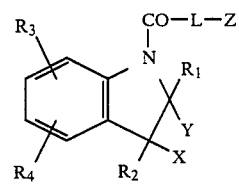

wherein
L is NH or O;
X and Y are independently selected from hydrogen or $C_{1-4}$ alkyl, or together are a bond;
$R_1$ and $R_2$ are independently selected from hydrogen, $C_{1-6}$ alkyl, $C_{2-6}$ alkenyl-$C_{1-4}$ alkyl, or together are $C_{2-4}$ polymethylene;
$R_3$ and $R_4$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl), hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;
Z is a group of formula (a), (b) or (c)

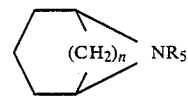

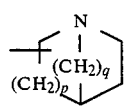

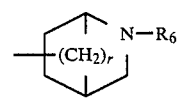

wherein
n is 2 or 3;
p is 1 or 2;
q is 1 to 3;
r is 1 to 3; and
$R_5$ or $R_6$ is $C_{1-7}$ alkyl, $C_{3-8}$ cycloalkyl, $C_{3-8}$ cycloalkyl-$C_{1-2}$ alkyl or $C_{2-7}$ alkenyl-$C_{1-4}$ alkyl;
having 5-HT M-receptor antagonist activity.

12 Claims, No Drawings

CERTAIN 2,3-DIHYDRO-INDOLE-1-CARBOXAMIDO-N-[8-AZABICYCLO(3.2.1)OCTAN-3-YL]DERIVATIVES HAVING 5-HT-ANTAGONIST ACTIVITY

This is a continuation-in-part of Ser. No. 000,550, filed Jan. 5, 1987, now abandoned.

This invention relates to novel compounds having useful pharmacological properties, to pharmaceutical compositions containing them, to a process and intermediates for their preparation, and to their use as pharmaceuticals.

The compound, N-(1-azabicyclo[2.2.2]oct-3-yl)-2,3-dihydroindole-1-carboxylic acid ester, (Compound 13) is disclosed in Nilsson et al, Acta Pharm. Suecica 5, 71–76 (1968), as an anticholinergic agent.

GB 2100259A and 2125398A, and EP-A-158265 describe benzoates and benzamides having an azabicyclic side chain and possessing 5-HT antagonist activity.

A class of novel, structurally distinct compounds has now been discovered. These compounds, together with Compound 13, have 5-HT M-receptor antagonist activity, anti-emetic activity and/or gastric motility enhancing activity.

Accordingly, the present invention provides a compound of formula (I), or a pharmaceutically acceptable salt thereof:

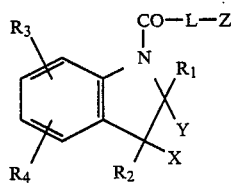

wherein
L is NH or O;
X and Y are independently selected from hydrogen or $C_{1-4}$ alkyl, or together are a bond;
$R_1$ and $R_2$ are independently selected from hydrogen, $C_{1-6}$ alkyl, $C_{2-6}$ alkenyl-$C_{1-4}$ alkyl, or together are $C_{2-4}$ polymethylene;
$R_3$ and $R_4$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;
Z is a group of formula (a), (b) or (c)

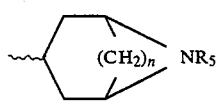

(a)

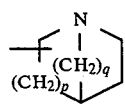

(b)

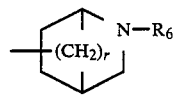

(c)

wherein
n is 2 or 3;
p is 1 or 2;
q is 1 to 3;
r is 1 to 3; and
$R_5$ or $R_6$ is $C_{1-7}$ alkyl, $C_{3-8}$ cycloalkyl, $C_{3-8}$ cycloalkyl-$C_{1-2}$ alkyl or $C_{2-7}$ alkenyl-$C_{1-4}$ alkyl;
with the proviso that the compound of formula (I) is other than Compound 13.

Preferably L is NH.
Suitable values for X and Y include hydrogen, methyl, ethyl, n- and iso-propyl; or together are a bond.
Often X and Y are both hydrogen.

Suitable values for $R_1$ or $R_2$ include hydrogen, methyl, ethyl, n- and iso-propyl; prop-2-enyl, but-2-enyl, but-3-enyl, 1-methylenepropyl and 1-methylprop-2-yl in their E and Z forms where stereoisomerism exists; or $R_1$ and $R_2$ together are as defined in formula (I). Often $R_1$ and $R_2$ are both hydrogen.

Values for $R_3$ and/or $R_4$ include hydrogen, fluoro, chloro, bromo, $CF_3$, methyl, ethyl methoxy, ethoxy, methylthio, ethylthio, acetyl, propionyl, acetylamino, methylsulphonylamino, methylsulphinyl, hydroxy, nitro; and amino, aminocarbonyl, aminosulphonyl, aminosulphonylamino or N-(aminosulphonyl)-methylamino any of which may be optionally substituted by one or two methyl groups or by a cyclopentyl or cyclohexyl group or disubstituted by $C_4$ or $C_5$ polymethylene; $R_3$ is often hydrogen and $R_4$ is hydrogen or a 5-substituent, such as halo or methoxy.

Preferably n is 2 or 3 and p, q and r are 1 or 2.
Examples of $R_5/R_6$ when $C_{1-7}$ alkyl include as groups of interest $C_{1-3}$ alkyl such as methyl, ethyl and n- and iso-propyl. Within $C_{1-7}$ alkyl, $C_{4-7}$ alkyl are also of interest, especially those of the formula $(CH_2)_u R_9$ wherein u is 1 or 2 and $R_9$ is a secondary or tertiary $C_{3-6}$ alkyl group. Examples of $C_{4-7}$ alkyl include n-, sec- and tert-butyl, n-pentyl, n-heptyl, and iso-butyl, 3-methylbutyl, and tert-butylmethyl.

Examples of $R_5/R_6$ when $C_{3-8}$ cycloalkyl-$C_{1-2}$ alkyl include in particular those wherein the cycloalkyl moiety is cyclohexyl or cyclopropyl. Examples include cyclopropylmethyl, cyclobutylmethyl, cyclopentylmethyl, cyclohexylmethyl, cyclopropylethyl, cyclobutylethyl, cyclopentylethyl, cyclohexylethyl, tert-butylmethyl, iso-propylmethyl, iso-propylethyl and tert-butylethyl.

$R_5/R_6$ may in particular be cyclopropylmethyl, cyclohexylmethyl, iso-propylmethyl, tert-butylmethyl or iso-propylethyl, preferably tert-butylmethyl.

Examples of $R_5/R_6$ when $C_{2-7}$ alkenyl-$C_{1-4}$ alkyl include prop-2-enyl, but-2-enyl, but-3-enyl, 1-methylenepropyl and 1-methyl-prop-2-enyl in their E and Z forms when stereoisomerism exists.

$R_5/R_6$ is preferably methyl or ethyl, most preferably methyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, lactic, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_{10}$-T wherein $R_{10}$ is $C_{1-6}$ alkyl, phenyl-$C_{1-6}$ alkyl or $C_{5-7}$ cycloalkyl, and T is a radical corresponding to an anion of an acid. Suitable examples of $R_{10}$ include methyl, ethyl and n- and iso-propyl; and benzyl and phenethyl. Suitable examples of T include halides such as chloride, bromide and iodide.

The compounds of formula (I) may also form internal salts such as pharmaceutically acceptable N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of formula (I) may adopt an endo or exo configuration with respect to L. The endo configuration is preferred.

A group of compounds within formula (I) is of formula (II):

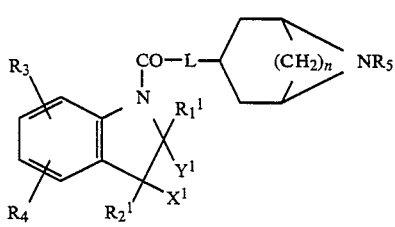
(II)

wherein $X^1$ and $Y^1$ are independently hydrogen, methyl or ethyl, or together are a bond, $R_1^1$ and $R_2^1$ are independently hydrogen, methyl or ethyl and the remaining variables are as defined in formula (I).

Examples of the variables and preferred variables are as so described for corresponding variables in relation to formula (I).

A further group of compounds within formula (I) is of formula (III):

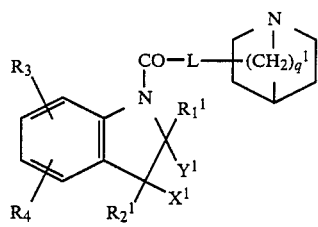
(III)

wherein $q^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

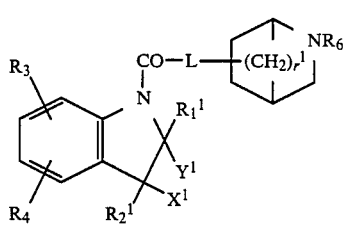
(IV)

wherein $r^1$ is 1 or 2 and the remaining variables are as defined in formulae (I) and (II).

Examples of the variables and preferred variables are as described for the corresponding variables in formula (I).

The invention also provides a process for the preparation of a compound of formula (I), or a pharmaceutically acceptable salt thereof, which process comprises reacting a compound of formula (V):

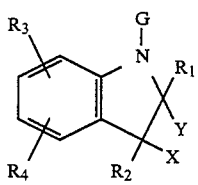
(V)

with a compound of formula (VI):

$$J\text{-}Z^1 \qquad (VI)$$

wherein

G is $COQ_1$, where $Q_1$ is a leaving group, or hydrogen; and, when G is $COQ_1$, J is $NH_2$, or OH or a reactive derivative thereof or, when G is hydrogen, J is a group containing an activated carbonyl group capable of forming a CO—L-linkage with the compound of formula (V); $Z^1$ is Z as defined or wherein $R_5/R_6$ is replaced by a hydrogenolysable protecting group; and the remaining variables are as hereinbefore defined; and thereafter optionally converting any $R_3$ and $R_4$ group to another $R_3$ and $R_4$ group respectively, converting $Z^1$, when other than Z, to Z; converting X and Y to other X and Y, and optionally forming a pharmaceutically acceptable salt of the resultant compound of formula (I).

Examples of leaving groups $Q_1$, displaceable by a nucleophile, include halogen such as chloro and bromo;

$C_{1-4}$ alkoxy, such as $CH_3O$ and $C_2H_5O$—; PhO—; activated hydrocarbyloxy, such as $Cl_5C_6O$— or $Cl_3CO$—; succinimidyloxy; and imidazolyloxy. Preferably $Q_1$ is halogen, most preferably chloro.

If a group $Q_1$ is a halide or imidazolyloxy, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group $Q_1$ is $C_{1-4}$ alkoxy, phenoxy, activated hydrocarbyloxy or succinimidyloxy then the reaction is preferably carried out in an inert polar solvent, such as toluene or dimethylformamide. In this instance, it is preferred that the group $Q_1$ is $Cl_3CO$— or succinimidyloxy and that the reaction is carried out in toluene at reflux temperature.

When J is OH or a reactive derivative thereof, the reactive derivative is often a salt, such as the lithium, sodium or potassium salt.

When G is hydrogen, $J-Z^1$ may be a compound of formula (VII) or (VIII) when L is NH; or of formula (IX) when L is O:

  (VII)

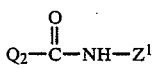  (VIII)

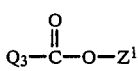  (IX)

wherein $Z^1$ is as hereinbefore defined, and $Q_2$ and $Q_3$ are leaving groups, preferably $Cl_3CO$ and Cl respectively.

When $J-Z^1$ is of formula (VII), the reaction is preferably carried out in an inert solvent, under conventional conditions 0°–100° C.

$Q_2$ is a leaving group as defined for $Q_1$ hereinbefore; and the reaction is carried out in accordance with the conditions described herein for the reaction wherein G is $COQ_1$.

Examples of $Q_3$, displaceable by a nucleophile, include halogen, such as chloro and bromo; and activated hydrocarbyloxy, such as $Cl_5C_6O$— and $Cl_3CO$.

If a group $Q_3$ is a halide, the reaction is carried out as described above for $Q_1$ halide.

If $Q_3$ is activated hydrocarbyloxy, the reaction is carried out as described for $Q_1$ activated hydrocarbyloxy.

It will be apparent that compounds of the formula (I) containing an $R_3$ or $R_4$ group which is convertible to another $R_3$ or $R_4$ group are useful novel intermediates. A number of such conversions is possible not only for the end compounds of formula (I), but also for their intermediates as follows:

(i) a hydrogen substituent is convertible to a nitro substituent by nitration;

(ii) a nitro substituent is convertible to an amino substituent by reduction;

(iii) a $C_{1-7}$ acylamino substituent is convertible to an amino substituent by deacylation;

(iv) an amino substituent is convertible to a $C_{1-4}$ acylamino substituent by acylation with a carboxylic acid derivative;

(v) a hydrogen substituent is convertible to a halogen substituent by halogenation;

(vi) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;

(vii) an amino, aminocarbonyl, aminosulphonyl, aminosulphonylamino or N-(aminosulphonyl)-N-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkoxy and nitro, or disubstituted by $C_{4-5}$ polymethylene, by N-alkylation;

(viii) an amino substituent is convertible to a $C_{1-6}$ alkylsulphonylamino group or an aminosulphonylamino group optionally N-substituted as defined by acylation with a $C_{1-6}$ alkylsulphonyl chloride or with a di-substituted aminosulphonyl chloride.

(ix) A $C_{1-4}$ alkylamino substituent group is convertible to an N-($C_{1-6}$ alkylsulphonyl)N-$C_{1-4}$ alkylamino group or an N-(amino sulphonyl)N-$C_{1-4}$ alkylamino group optionally N-substituted as defined by acylation with a $C_{1-6}$ alkylsulphonyl chloride or di-substituted aminosulphonyl chloride.

Conversions (i) to (ix) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv), (viii), and (ix) the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the N- moiety of a side chain (a), (b) or (c) and suitable precautions will routinely be taken by those skilled in the art.

In regard to (vii), alkylation is carried out with a corresponding alkylating agent such as the chloride or bromide under conventional conditions.

$Z^1$ when other than Z may have a hydrogenolysable protecting group which is benzyl optionally substituted by one or two groups as defined for $R_3$ and $R_4$. Such benzyl groups may, for example, be removed, when $R_3$ or $R_4$ is not halogen, by conventional transition metal catalysed hydrogenolysis to give compounds of the formula (X):

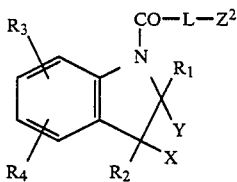 (X)

wherein $Z^2$ is of formula (d) or (e)

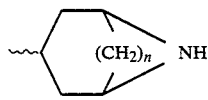 (d)

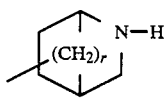 (e)

wherein the variables are as defined in formula (I).

This invention also provides a further process for the preparation of a compound of the formula (I) which comprises N-alkylating a compound of formula (X), and optionally forming a pharmaceutically acceptable salt, of the resulting compound of the formula (I).

In this further process of the invention 'N-alkylation' comprises the substitution of the N-atom depicted in formula (X) by any group $R_5/R_6$ as hereinbefore defined. This may be achieved by reaction of the compound of formula (X) with a compound $R_5Q_4$ or $R_6Q_4$ wherein $R_5$ and $R_6$ are as hereinbefore defined and $Q_4$ is a leaving group.

Suitable values for $Q_4$ include groups displaced by nucleophiles, such as Cl, Br, I, $OSO_2CH_3$ or $OSO_2C_6H_4pCH_3$.

Favoured values for $Q_4$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slight above.

Alternatively, 'N-alkylation' may be effected under conventional reductive alkylation conditions when the group $R_5$ or $R_6$ in the compound of formula (I) contains a methylene group adjacent to the N-atom in the bicycle.

Interconverting $R_5$ or $R_6$ in the compound of the formula (X) before coupling with the compound of the formula (V) is also possible. Such interconversions are effected conveniently under the above conditions. It is desirable to protect any amine function with a group readily removable by acidolysis, such as a $C_{2-7}$ alkanoyl group, before $R_5/R_6$ interconversion.

When $R_5$ or $R_6$ in the compound of formula (VI) contains a methylene group adjacent to the N-atom in the bicycle it is often convenient in the preparation of such a compound of formula (VI) to prepare the corresponding compound wherein the methylene group is replaced by —CO—, or for $R_5$ or $R_6$ is methyl, where the methyl group is replaced by esterified carboxyl. Such compounds may then be reduced using a strong reductant such as lithium aluminium hydride to the corresponding compound of formula (V).

The compounds of formula (V) and (VI) are known or are preparable analogously to, or routinely from, known compounds. Intermediates of formula (V) wherein G is H and X and Y are hydrogen may be prepared from the corresponding intermediate wherein X and Y are a bond. Intermediates of formula (V) wherein G is $COQ_1$ form an aspect of the invention.

Compounds of the formula (VI) wherein Z is of formula (c) may be prepared as described in European Patent Publication No. 115933 or by analogous method thereto.

Compounds of the formula (X) are novel and form an aspect of the invention.

It will be realised that in the compound of the formula (I) the —CO—L—linkage may have an endo or exo orientation with respect to the ring of the bicyclic moiety to which it is attached. A mixture of endo and exo isomers of the compound of the formula (I) may be synthesised non-stereospecifically and the desired isomer separated conventionally therefrom, for example by chromatography; or alternatively the endo and exo isomer may if desired be synthesised from the corresponding endo or exo form of the compound of the formula (VI).

Compounds of the formula (I) wherein X and Y are both hydrogen may be converted to the corresponding compounds wherein X and Y are a bond by conventional oxidation, and this is the preferred method of preparation when X and Y are a bond. Compounds of the formula (I) wherein X and Y are a bond may be converted to the corresponding compounds wherein X and Y are hydrogen by reduction; however it is preferred that this is carried out on the compound of formula (V) wherein G is H prior to coupling.

Pharmaceutically acceptable salts of the compounds of this invention may be formed conventionally. The acid addition salts may be formed for example by reaction of the base compound of formula (I) with a pharmaceutically acceptable organic or inorganic acid.

The compounds of the present invention are 5-HT antagonists and it is thus believed may generally be used in the treatment or prophylaxis of migraine, cluster headaches and trigeminal neuralgia. Compounds which are 5-HT antagonists may also be of potential use in the treatment of CNS disorders such as anxiety and psychosis; arrhythmia, obesity and irritable bowel syndrome.

The compounds of the present invention also have anti-emetic activity; in particular that of preventing cytotoxic agent- or radiation- induced nausea and vomiting. Examples of cytotoxic agents include cisplatin, doxorubicin and cyclophosphamide.

The compounds of the present invention also have gastric motility enhancing activity, useful in the treatment of disorders such as retarded gastric emptying, dyspepsia, flatulence, oesophagal reflux and peptic ulcer.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of migraine, cluster headache, trigeminal neuralgia and/or emesis in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contan 0.005 to 1000 mg for example 0.01 to 50 mg, of the compound of the invention. Unit doses may be administered one or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I); the following descriptions illustrate the preparation of intermediates.

N.B. Nomenclature is based on Chemical Abstracts Index Guide 1977 published by the American Chemical Society.

Description 1

1-(2,3-Dihydro)-indolyltrichloromethyl carbamate (D1)

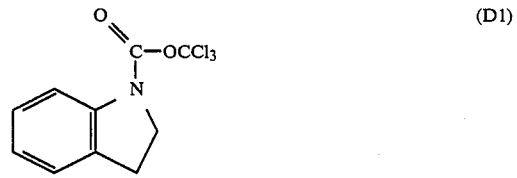

To 2,3-dihydroindole (5 g) in dry dichloromethane (140 ml) and triethylamine (5.85 ml) at 0° was added dropwise trichloromethyl chloroformate (5 ml) in dry dichloromethane (20 ml). The reaction mixture was stirred at room temperature for 2 h, then washed with water (5 ml) and 5N hydrochloric acid solution (5 ml). The organic phase was dried ($Na_2SO_4$), the solvent evaporated in vacuo and the residue purified by filtration through a short alumina column, eluting with dichloromethane to give the title compound (D1) (8.5 g, 72%) as a buff solid m.p. 59°–60°.

$^1$H-NMR (CDCl$_3$) 60 MHz: δ 7.85–7.55 (m, 1H), 7.30–6.70 (m, 3H), 4.25–3.70 (m, 2H), 3.25–2.80 (m, 2H).

Description 2

2,3-Dihydro-3-methylindole (D2)

Following the procedure outlined by G. W. Gribble and J. H. Hoffman, Synthesis, 859, 1977, 3-methyl indole (5 g) was converted to the title compound (D2) (4.17 g, 82%).

¹H NMR (CDCl₃) 60 MHz δ 7.30–6.30 (m, 4H), 3.80–2.80 (m, 4H), 1.30 (d, 3H).

Description 3

2,3-Dihydro-5-fluoroindole (D3)

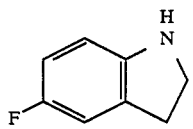
(D3)

Following the procedure outlined in Description 2, 5-fluoroindole (3 g) was converted to the title compound (D3) (2.54 g, 84%).

¹H-NMR (CDCl₃) 60 MHz: δ 7.05–6.10 (m, 3H), 4.10–2.60 (m, 5H).

Description 4

2,3-Dihydro-5-chloroindole (D4)

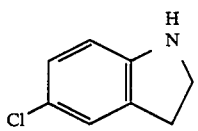
(D4)

Following the procedure outlined in Description 2, 5-chloroindole (0.86 g) was converted to the title compound (D4) (0.84 g, 97%).

¹H-NMR (CDCl₃) 60 MHz: δ 7.30–6.65 (m, 2H), 6.60–6.25 (m, 1H), 4.10–3.25 (m, 3H), 3.20–2.70 (m, 2H).

Description 5

2,3-Dihydro-5-methoxyindole (D5)

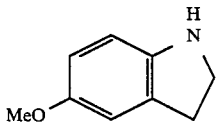
(D5)

A solution of 5-methoxyindole (1 g) in glacial acetic acid (20 ml) was hydrogenated over platinum oxide (0.27 g) at room temperature. After absorption of the theoretical amount of hydrogen (153 ml), the catalyst was filtered off and the solvent evaporated in vacuo. The residue was basified with saturated potassium carbonate solution and extracted with diethyl ether. The organic phase was dried (Na₂SO₄), the solvent evaporated in vacuo to give the title compound (D5) (0.43 g, 42%).

¹H-NMR (CDCl₃) 60 MHz: δ 6.85–6.35 (m, 3H), 3.65 (s, 3H), 3.60–2.70 (m, 5H).

Description 6

2,3-Dihydro-3-ethylindole (D6)

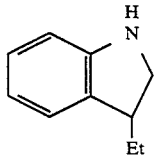
(D6)

Following the procedure outlined in Description 2, 3-ethylindole (2.3 g) (J. T. Fitzpatrick and R. D. Hiser, J. Org. Chem., 22, 1703–4, 1957) was converted to the title compound (D6) (1.3 g, 56%).

¹H-NMR (CDCl₃) 60 MHz: δ 7.20–6.40 (m, 4H), 3.90–2.90 (m, 4H), 2.10–0.8 (m, 2H), 0.9 (t, 3H).

Description 7

1-(2,3-Dihydro-3-methyl)indolyl-O-(1-succinimidyl)-carbamate (D7)

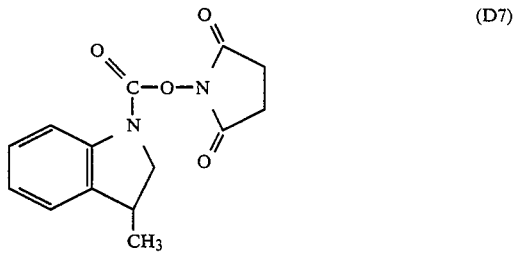
(D7)

N,N-Disuccinimidyl carbonate (8.03 g) and 2,3-dihydro-3-methylindole (D2) (4.17 g) in dry toluene (150 ml) was stirred at room temperature overnight. The solvent was evaporated in vacuo and the residue dissolved in dichlormethane, washed with 5N hydrochloric acid solution (10 ml), saturated potassium bicarbonate (10 ml) and brine (30 ml). The organic phase was dried (Na₂SO₄), evaporated in vacuo and the residue purified by filtration through a short silica column, eluting with dichloromethane to give the title compound (D7) (6.85 g, 80%).

¹H-NMR (CDCl₃) 60 MHz: δ 7.85–6.80 (m, 4H), 4.60–4.00 (m, 1H), 3.95–3.10 (m, 2H), 2.75 (s, 4H), 1.30 (bd, 3H).

Description 8

1-(2,3-Dihydro-5-fluoro)indolyl-O-(1-succinimidyl)carbamate (8)

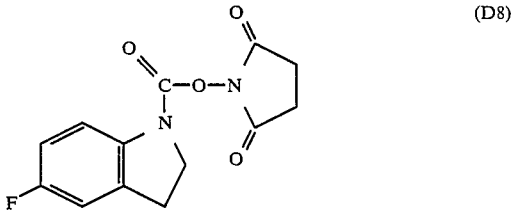
(D8)

Following the procedure outlined in Description 7, reaction of N,N-disuccinimidyl carbonate (4.75 g) with 2,3-dihydro-5-fluoroindole (D3) afforded the title compound (D8) (5 g, 97%).

¹H-NMR (CDCl₃) 60 MHz: δ 7.90–7.60 (m, 1H), 7.30–6.60 (m, 3H), 4.40–4.00 (m, 2H), 3.40–2.90 (m, 2H), 2.85 (s, 4H).

Description 9

1-(2,3-Dihydro-5-methoxy)indolyl trichloromethyl carbamate (D9)

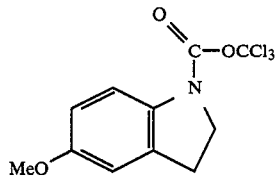

Following the procedure outlined in Description 1, reaction of 2,3-dihydro-5-methoxyindole (D5) (0.43 g) with trichloromethylchloroformate (0.35 ml) afforded the title compound (D9) (0.52 g, 58%).

$^1$H-NMR (CDCl$_3$) αMHz δ 7.88–7.58 (m, 1H), 6.85–6.48 (m, 2H), 4.35–3.80 (m, 2H), 3.70 (s, 3H), 3.35–2.80 (m, 2H).

Description 10

1-(2,3-Dihydro)indolylcarbonyl chloride (D10)

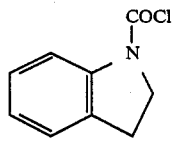

To phosgene [110 ml (12.5% w/w solution in toluene)] in dry dichloromethane (150 ml) at 0° was added dropwise a solution of triethylamine (17 ml) and freshly distilled 2,3-dihydroindole (14.5 g) in dry dichloromethane (100 ml). The reaction mixture was then stirred at 0° for 1 h, and then poured into pentane (2.5l), washed with 5N sulphuric acid solution (100 ml) and brine (100 ml). The organic phase was dried (Na$_2$SO$_4$), the solvent evaporated in vacuo and the residue triturated with 60/80 pet. ether to give the title compound (D10) (18.37 g, 83%).

Description 11

1-(2,3-Dihydro-3-ethyl)indolylcarbonyl chloride (D11)

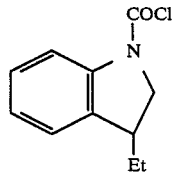

Following the procedure outlined in Description 10, reaction of 2,3-dihydro-3-ethylindole (D6) (1.25 g) with phosgene [7.7 ml (12.5% w/w solution in toluene)] afforded the title compound (D11) (1.6 g, 90%).

Description 12

1-(2,3-Dihydro-5-nitro)indolyl-trichloromethyl carbamate (D12)

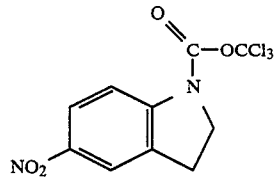

Following the procedure outlined in Description 1, reaction of 2,3-dihydro-5-nitroindole (4.72 g) with trichloromethylchloroformate (3.44 ml) afforded the title compound (D12) (5.5 g, 59%)

$^1$H-NMR (CDCl$_3$) 60 MHz: δ 8.80–7.10 (m, 3H), 4.70–3.90 (m, 2H), 3.50–2.95 (m, 2H).

Description 13

1-[1-(2,3-Dihydro-6-nitro)indolylcarbonyl]imidazole (D13)

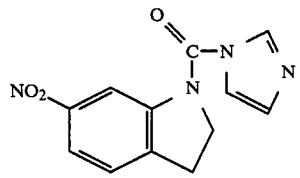

2,3-Dihydro-6-nitroindole (3 g) and 1,1'-carbonyldiimidazole (2.96 g) in dry toluene (75 ml) was heated under reflux for 5 h. The reaction mixture was cooled and the solvent evaporated in vacuo. The residue was dissolved in dichloromethane (100 ml) and washed with 5N hydrochloric acid solution (10 ml) and water (20 ml). The organic phase was dried (Na$_2$SO$_4$) and the solvent evaporated in vacuo to give the title compound (D13) (4.7 g, 100%).

Description 14

1-(2,3-Dihydro-3,3-dimethyl)indolylcarbonyl chloride (D14)

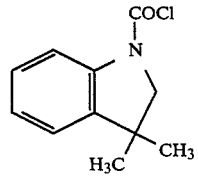

Following the procedure outlined in Description 10, reaction of 2,3-dihydro-3,3-dimethylindole (2.7 g) with phosgene [16.5 ml (12.5% w/w solution in toluene)] afforded the title compound (D14) (3.5 g, 91%).

Description 15
2,3-Dihydro-2,3-dimethylindole (D15)

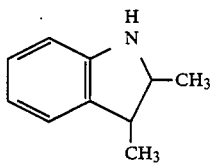

Following the procedure outlined by G. W. Gribble and J. H. Hoffman, Synthesis 859, 1977, 2,3-dimethylindole (4.2 g) was converted to the title compound as a mixture of isomers (D15) (3.66 g, 87%).

$^1$H-NMR (CDCl$_3$) 270 MHz: δ 7.10–6.95 (m, 2H), 6.75 (t, 1H), 6.60 (d, 1H), 3.95–3.85 (m, 0.2H), 3.80–3.35 (m, 1.8H), 3.32–3.15 (m, 0.2H), 2.90–2.75 (m, 0.8H), 1.35–1.25 (m, 4.8H), 1.20–1.10 (m, 1.2H).

Description 16
2,3-Dihydro-2,3,3-trimethylindole (D16)

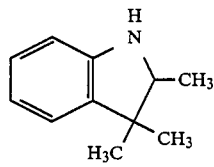

A solution of 2,3,3-trimethylindolenine (2 g) in glacial acetic acid (40 ml) was hydrogenated over platinum oxide (0.2 g) at ambient temperature. After absorption of the theoretical amount of hydrogen (282 ml), the catalyst was filtered off and the solvent was evaporated under reduced pressure. The residue was basified with saturated potassium carbonate and the product extracted into diethyl ether. The organic phase was dried (Na$_2$SO$_4$), and the solvent was evaporated under reduced pressure and the residue filtered through a short silica column eluting with 40% hexane/60% diethyl ether to give the title compound (D16) (1.8 g, 90%).

$^1$H-NMR (CDCl$_3$) 60 MHz: δ 7.50–6.40 (m, 4H), 3.80–3.20 (m, 2H), 1.20 (s, 6H), 1.00 (s, 3H).

Description 17
2,3-Dihydro-3-isopropylindole (D17)

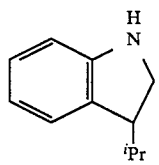

Following the procedure outlined in Description 15, 3-isopropylindole (3 g) (G. F. Smith and A. E. Walters, J. Chem. Soc. 940, 1961) was converted to the title compound (D17) (1.1 g, 36%).

$^1$H-NMR (CDCl$_3$) 60 MHz: δ 7.50–6.40 (m, 4H), 3.90–2.90 (m, 4H), 2.50–1.70 (m, 1H), 1.30–0.70 (m, 6H).

Description 18
1-(2,3-Dihydro-2-methyl)indolylcarbonyl chloride (D18)

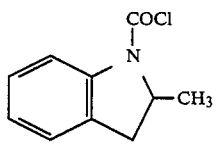

To phosgene [13.5 ml (12.5% w/w solution in toluene)] in dry dichloromethane (50 ml) at 0° C. was added dropwise a solution of triethylamine (2 ml) and freshly distilled 2,3-dihydro-2-methylindole (2 g) in dry dichloromethane (25 ml). The reaction mixture was stirred at 0° C. for 1 h and then poured into pentane (300 ml), washed with 5N sulphuric acid solution (20 ml) and brine (20 ml). The organic phase was dried (Na$_2$SO$_4$) and the solvent was evaporated under reduced pressure to give the title compound (D18) (2.7 g, 92%).

Description 19
1-(2,3-Dihydro-2,3-dimethyl)indolylcarbonyl chloride (D19)

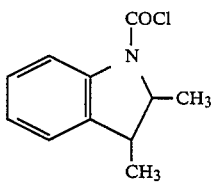

Following the procedure outlined in Description 18, reaction of 2,3-dihydro-2,3-dimethylindole (D1) (0.5 g) with phosgene [3.1 ml (12.5% w/w solution in toluene)] and triethylamine (0.47 ml) afforded the title compound (D19) (0.58 g, 82%).

Description 20
1-(2,3-Dihydro-2,3,3-trimethyl)indolylcarbonyl chloride (D20)

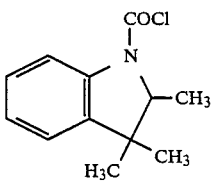

Following the procedure outlined in Description 18, reaction of 2,3-dihydro-2,3,3-trimethylindole (D2) (0.5 g) with phosgene [2.8 ml (12.5% w/w solution in toluene)] and triethylamine (0.43 ml) afforded the title compound (D20) (0.6 g, 87%).

Description 21

1-(2,3-Dihydro-3-isopropyl)indolylcarbonyl chloride (D21)

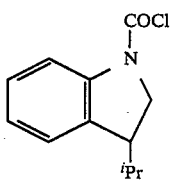

Following the procedure outlined in Description 18 reaction of 2,3-dihydro-3-isopropylindole (D3) (1.1 g) with phosgene [6.2 ml (12.5% w/w solution in toluene)] and triethylamine (0.95 ml) afforded the title compound (D21) (1.53 g, 100%).

Description 22

1-(2,3,4,4a,9,9a-hexahydro)carbazolylcarbonyl chloride (D22)

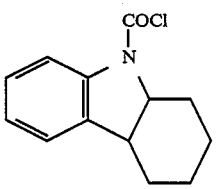

Following the procedure outlined in Description 18, 2,3,4,4a,9,9a-hexahydro-1H-carbazole (0.7 g) (G. W. Gribble and J. H. Hoffman, Synthesis 859, 1977) was converted to the title compound (D22) 0.44 g.

EXAMPLE 1 endo-N-(9-Methyl-9-azabicyclo[3.3.1]non-3-yl)-2,3-dihydroindole-1-carboxamide (E1)

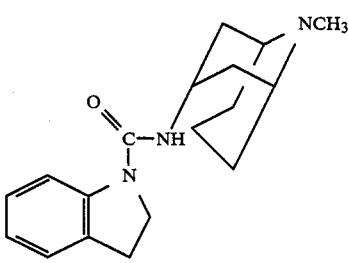

To 1-(2,3-dihydro)-indolyltrichloromethyl carbamate (D1) (3.64 g) in dry toluene (100 ml) was added endo-3-amino-9-methyl-9-azabicyclo[3.3.1]nonane (2 g) in dry toluene (20 ml). The reaction mixture was heated under reflux for 24 h, then the solvent evaporated in vacuo. The residue was extracted with dichloromethane (200 ml) and washed with saturated potassium carbonate solution (2×20 ml). The organic phase was dried (Na$_2$SO$_4$) concentrated and the residue purified by column chromatography on alumina, eluting with CHCl$_3$ to give, after crystallisation from ethyl acetate, the title compound (E1) (2 g, 52%) m.p. 176°–8°.

$^1$H-NMR (CDCl$_3$) 270 MHz: δ 7.85 (d, 1H), 7.25–7.05 (m, 2H), 6.95–6.85 (m, 1H), 4.45–4.25 (m, 2H), 4.00–3.80 (t, 2H), 3.25–3.05 (m, 4H), 2.65–2.40 (m, 2H), 2.50 (s, 3H), b 2.15–1.85 (m, 3H), 1.65–1.00 (m, 5H).

EXAMPLE 2 endo-N-(8-Methyl-8-azabicyclo[3.2.1]oct-3-yl)-2,3-dihydroindole-1-carboxamide (E2)

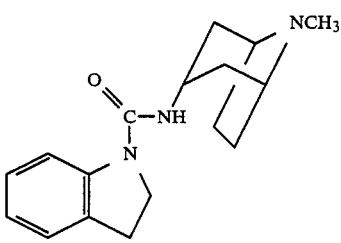

Following the procedure outlined in Example 1, reaction of 1-(2,3-dihydro)-indolyltrichloromethyl carbamate (D1) (0.64 g) with endo-3-amino-8-methyl-8-azabicyclo[3.2.1]octane (0.32 g) afforded the title compound (E2) m.p. 153°–4°

$^1$H-NMR (CDCl$_3$) 270 MHz: δ 7.85 (d, 1H), 7.25–7.10 (m, 2H), 6.95–6.85 (m, 1H), 4.95 (bd, 1H), 4.10 (q, 1H), 3.90 (t, 2H), 3.25–3.10 (m, 4H), 2.40–2.05 (m, 4H), 2.30 (s, 3H), 1.90–1.75 (m, 4H).

EXAMPLE 3 endo(8-Methyl-8-azabicyclo[3.2.1]oct-3-yl)-2,3-dihydroindole carboxylic acid ester (E3)

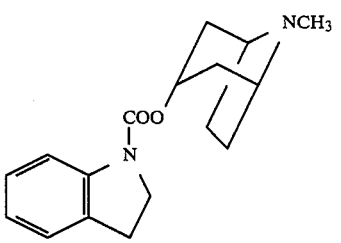

To 3-tropanol (1.13 g) in diglyme (50 ml), was added portionwise potassium t-butoxide (0.94 g). The reaction mixture was stirred under an atmosphere of N$_2$ at room temperature for 1 h and then the solvent was evaporated in vacuo. The resultant gum was redissolved in diglyme (50 ml) and 1-(2,3-dihydro)indole trichloromethyl carbamate (D1) (1.5 g) was added. The reaction mixture was heated under reflux for 36 h, then cooled and evaporated in vacuo. The residue was dissolved in 5N hydrochloric acid solution (10 ml) and washed with diethyl ether (30 ml). The aqueous phase was basified with potassium carbonate and extracted with dichloromethane (3×75 ml). The organic phase was dried (Na$_2$SO$_4$), the solvent evaporated in vacuo and the residue purified by column chromatography on alumina eluting with dichloromethane to give, after crystallisation from diethyl ether the title compound (E3) (0.5 g, 31%). m.p. 133°–4°.

$^1$H-NMR (CDCl$_3$) 270 MHz: δ 7.85 (bd, 1H), 7.22–7.12 (m, 2H), 7.00–6.92 (m, 1H), 5.05 (t, 1H), 4.06 (t, 2H), 3.28–3.08 (m, 4H), 2.32 (s, 3H), 2.32–1.75 (m, 8H).

EXAMPLE 4 endo-N-(8-Methyl-8-azabicyclo[3.2.1]oct-3-yl)-2,3-dihydro-3-methylindole-1-carboxamide hydrochloride (E4)

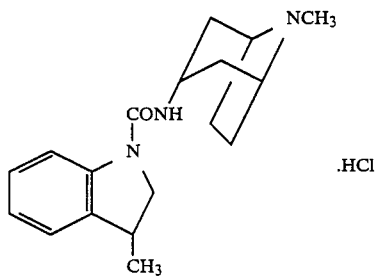

Triethylamine (1.8 ml), 1-(2,3-dihydro-3-methyl)indolyl-O-(1-succinimidyl)carbamate (D7) (3.5 g) and endo-3-amino-8-azabicyclo[3.2.1]octane (1.8 g) were dissolved in dry toluene (100 ml) and heated under reflux overnight. The reaction mixture was cooled and the solvent evaporated in vacuo. The residue was extracted with dichloromethane (200 ml) and washed with saturated potassium carbonate solution (2×20 ml). The organic phase was dried ($Na_2SO_4$), concentrated and the residue purified by column chromatography on alumina, eluting with chloroform. The product was isolated as the hydrochloride salt (E4) (0.97 g, 23%). m.p. 268°–70°.

$^1$H-NMR ($d_6$-DMSO) 270 MHz: 10.35–10.05 (m, 1H), 7.75 (d, 1H), 7.25–7.05 (m, 2H), 6.95–6.85 (m, 1H), 6.29 (bs, 1H), 4.15 (t, 1H), 3.90–3.70 (m, 3H), 3.65–3.30 (m, 2H), 2.65 (s, 3H), 2.50–2.10 (m, 8H), 1.26 (d, 3H).

EXAMPLE 5 endo-N-(8-Methyl-8-azabicyclo[3.2.1]oct-3-yl)-2,3-dihydro-3,3-dimethylindole-1-carboxamide (E5)

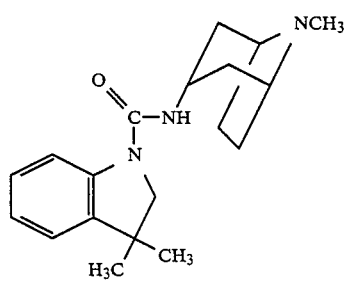

Following the procedure outlined in Example 14, reaction of 1-(2,3-dihydro-3,3-dimethyl)indolylcarbonyl chloride (D14) (1.2 g) with endo-3-amino-8-azabicyclo[3.2.1]octane (0.8 g) afforded the title compound (E5) (0.88 g, 50%) m.p. 158°–9°.

$^1$H-NMR $CDCl_3$: 7.80 (d, 1H), 7.25–7.05 (m, 2H), 7.00–6.90 (m, 1H), 6.92 (bd, 1H), 4.08 (q, 1H), 3.60 (s, 2H), 3.30–3.15 (m, 2H), 2.35 (s, 3H), 2.40–2.10 (m, 4H), 1.95–1.65 (m, 4H), 1.35 (s, 6H).

EXAMPLE 6 endo-N-(8-Methyl-8-azabicyclo[3.2.1]oct-3-yl)-3-methylindole-1-carboxamide hydrochloride (E6)

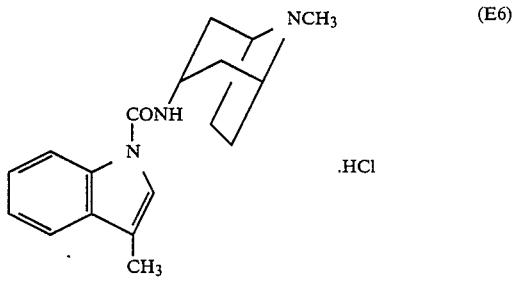

endo-N-(8-Methyl-8-azabicyclo[3.2.1]oct-3-yl)-2,3-dihydro-3-methylindole-1-carboxamide hydrochloride (E4) (0.5 g) and 2,3-dichloro-5,6-dicyano-1,4-benzoquinone (0.41 g) in dry chloroform (100 ml) were heated under reflux for 6 h. The reaction mixture was cooled and washed with saturated potassium carbonate solution (20 ml). The organic phase was dried ($Na_2SO_4$), concentrated and the residue filtered through a short alumina column, eluting with chloroform. The product was isolated as the hydrochloride salt (E6) (0.2 g, 40%). m.p. 158°–61°

$^1$H-NMR ($d_6$-DMSO) 400 MHz: δ 10.50 (bs, 1H), 8.15 (d, 1H), 7.85 (bs, 1H), 7.65 (s, 1H), 7.55 (d, 1H), 7.30–7.15 (m, 2H), 4.00–3.75 (m, 3H), 2.65 (bs, 3H), 2.50–2.05 (m, 11H).

EXAMPLE 7 endo-N-(8-Ethyl-8-azabicyclo[3.2.1]oct-3-yl)-2,3-dihydroindole-1-carboxamide (E7)

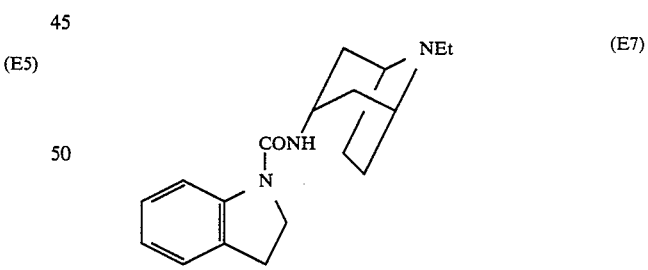

Following the procedure outlined in Example 1, reaction of 1-(2,3-dihydro)indole-trichloromethyl carbamate (D1) (0.91 g) with endo-3-amino-8-ethyl-8-azabicyclo[3.2.1]octane (0.5 g) afforded the title compound (E7) (0.24 g, 25%) m.p. 140°–1°.

$^1$H-NMR ($CDCl_3$) 270 MHz: δ 7.85 (d, 1H), 7.25–7.10 (m, 2H), 6.95–6.85 (m, 1H), 4.95 (bd, 1H), 4.10 (q, 1H), 3.90 (t, 2H), 3.35 (bs, 2H), 3.15 (t, 2H), 2.45 (q, 2H), 2.38–2.20 (m, 2H), 2.18–2.00 (m, 2H), 1.95–1.65 (m, 4H), 1.10 (t, 3H).

EXAMPLE 8 endo-N-(8-Methyl-8-azabicyclo[3.2.1]oct-3-yl)-5-fluoro-2,3-dihydroindole-1-carboxamide hydrochloride (E8)

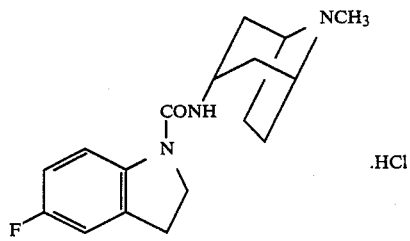

Following the procedure outlined in Example 4, reaction of 1-(2,3-dihydro-5-fluoro)indolyl-O-(1-succinimidyl)carbamate (D8) (3.5 g) with triethylamine (1.75 ml) and endo-3-amino-8-methyl-8-azabicyclo[3.2.1]octane (1.76 g) afforded the free base, which was converted to the hydrochloride salt (E8) (1.11 g, 18%) m.p. 299°–300° (decomposition).

$^1$H-NMR (d$_6$-DMSO) 270 MHz: δ 10.35–10.15 (m, 1H), 7.80–7.70 (m, 1H), 7.10–6.85 (m, 2H), 6.30 (bs, 1H), 4.05 (t, 2H), 3.90–3.70 (m, 3H), 3.10 (t, 2H), 2.65 (bs, 3H), 2.50–2.05 (m, 8H).

EXAMPLE 9 endo-N-(8-Methyl-8-azabicyclo[3.2.1]oct-3-yl)-2,3-dihydro-5-chloroindole-1-carboxamide (E9)

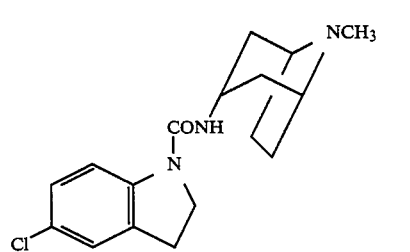

To phosgene [3.8 ml (12.5% w/w solution in toluene)] in dry dichloromethane (50 ml) was added dropwise 2,3-dihydro-5-chloroindole (D4) (0.83 g) in CH$_2$Cl$_2$ (20 ml). Triethylamine (0.83 ml) was then added and the whole stirred at room temperature for 10 min. endo-3-Amino-8-methyl-8-azabicyclo[3.2.1]octane (0.83 g) in dry dichloromethane (10 ml) was added and the reaction mixture stirred at room temperature for 2 h, then washed with saturated potassium bicarbonate solution (15 ml) and brine (20 ml). The organic phase was dried (Na$_2$SO$_4$), the solvent evaporated in vacuo and the residue column chromatographed on alumina eluting with chloroform to give, after crystallisation from ethyl acetate, the title compound (E9) (0.36 g, 19%) m.p. 149°–50°.

$^1$H-NMR (CDCl$_3$) 400 MHz: δ 7.81 (d, 1H), 7.15–7.05 (m, 2H), 4.90 (bd, 1H), 4.08 (q, 1H), 3.91 (t, 2H), 3.28–3.10 (m, 4H), 2.34 (s, 3H), 2.35–2.08 (m, 4H), 1.90–1.65 (m, 4H).

EXAMPLE 10 endo-N-(8-Methyl-8-azabicyclo[3.2.1]oct-3-yl)2,3-dihydro-5-methoxyindole-1-carboxamide (E10)

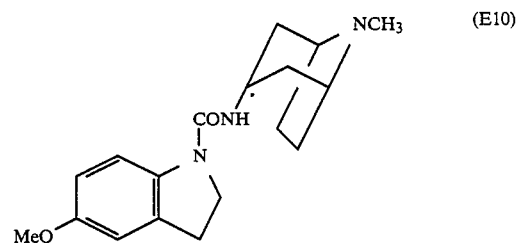

Following the procedure outlined in Example 1, reaction of 1-(2,3-dihydro-5-methoxy)indolyl trichloromethyl carbamate (D9) (0.48 g) with endo-3-amino-8-methyl-8-azabicyclo[3.2.1]octane (0.23 g) afforded the title compound (E10) (0.22 g, 45%) m.p. 142°–5°.

$^1$H-NMR (CDCl$_3$) 270 MHz: δ 7.75 (d, 1H), 6.80–6.65 (m, 2H), 4.88 (bd, 1H), 4.08 (q, 1H), 3.90 (t, 2H), 3.78 (s, 3H), 3.28–3.10 (m, 4H), 2.32 (s, 3H), 2.40–2.10 (m, 4H), 1.90–1.65 (m, 4H).

EXAMPLE 11 endo-N-(8-Methyl-8-azabicyclo[3.2.1]oct-3-yl)indole-1-carboxamide hydrochloride (E11)

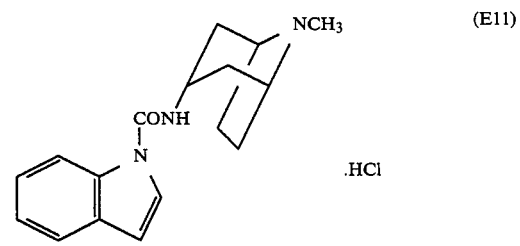

Following the procedure outlined in Example 6, reaction of endo-N-(8-methyl-8-azabicyclo[3.2.1]oct-3-yl)2,3-dihydroindole-1-carboxamide hydrochloride (E2) (0.46 g) and 2,3-dichloro-5,6-dicyano-1,4-benzoquinone (0.44 g) afforded the title compound (E11) (0.31 g, 68%) m.p. 258°–60° (decomposition).

$^1$H-NMR (d$_6$-DMSO) 270 MHz: δ 10.6–10.3 (m, 1H), 8.15–7.95 (m, 2H), 7.85 (d, 1H), 7.65–7.55 (m, 1H), 7.35–7.10 (m, 2H), 6.75–6.65 (m, 1H), 4.05–3.65 (m, 3H), 2.65 (bs, 3H), 2.60–2.00 (m, 8H).

EXAMPLE 12

N-(1-Azabicyclo[2.2.2]oct-3-yl)2,3-dihydroindole-1-carboxamide hydrochloride (E12)

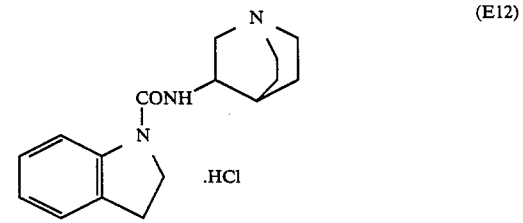

A mixture of 3-amino-1-azabicyclo[2.2.2]octane (0.5 g) and triethylamine (0.7 ml) in dry dimethylformamide (30 ml) was heated at 50° for 1 h. The solution was cooled and added dropwise to a solution of 1-(2,3-dihydro)indolylcarbonyl chloride (D10) (0.46 g) and triethylamine (0.35 ml) in dry dimethylformamide (50 ml) at 0°. The reaction mixture was stirred at room temperature for 2 h, the solvent was then evaporated in vacuo. The residue was dissolved in dichloromethane and washed with 10% sodium hydroxide solution (10 ml). The organic phase was dried (Na$_2$SO$_4$), the solvent evaporated in vacuo and the residue was column chromatographed on alumina, eluting with chloroform. The product was isolated as the hydrochloride salt (E12) (0.16 g, 21%) m.p. 138°–40°.

$^1$H-NMR (d$_6$-DMSO) 400 MHz: δ 10.7–10.3 (m, 1H), 7.82 (d, 1H), 7.16 (d, 1H), 7.08 (t, 1H), 6.86 (t, 1H), 6.80 (d, 1H), 4.18–4.08 (m, 1H), 4.06–3.92 (m, 2H), 2.54 (t, 1H), 2.46–3.04 (m, 7H), 2.18–2.06 (m, 2H), 1.96–1.78 (m, 2H), 1.76–1.60 (m, 1H).

EXAMPLE 13

N-(1-Azabicyclo[2.2.2]oct-3-yl)-2,3-dihydroindole-1-carboxylic acid ester (E13)

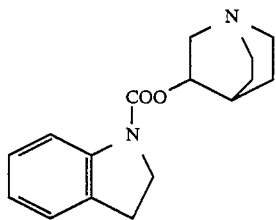

To 1-azabicyclo[2.2.2]octan-3-ol (1 g) in dry tetrahydrofuran (75 ml) at −78° under an atmosphere of nitrogen, was added dropwise n-butyl lithium [5.2 ml (1.6M solution in hexane)]. The mixture was allowed to warm to room temperature and then stirred for 10 min. The reaction mixture was cooled to −78° and 2,3-dihydroindole (1.43 g) in dry tetrahydrofuran (20 ml) was added dropwise. The reaction mixture was again allowed to warm to room temperature and stirred overnight. Water was added and the whole evaporated in vacuo, the residue was dissolved in dichloromethane (150 ml) and washed with saturated potassium carbonate solution (30 ml). The organic phase was dried (Na$_2$SO$_4$), the solvent was evaporated in vacuo and the residue column chromatographed on alumina, eluting with chloroform to give, after crystallisation from ethyl acetate, the title compound (E13) (0.29 g, 14%) m.p. 124°–5°.

$^1$H-NMR (CDCl$_3$) 270 MHz: δ 8.00–7.70 (m, 1H), 7.30–7.10 (m, 2H), 7.05–6.90 (m, 1H), 5.05–4.80 (m, 1H), 4.20–3.95 (m, 2H), 3.45–3.25 (m, 1H), 3.25–2.50 (m, 7H), 2.30–2.05 (m, 1H), 2.05–1.20 (m, 4H).

EXAMPLE 14 endo-N-(8-Methyl-8-azabicyclo[3.2.1]oct-3-yl)-2,3-dihydro-3-ethylindole-1-carboxamide hydrochloride (E14)

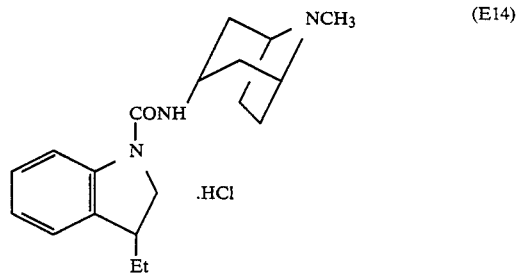

To 1-(2,3-dihydro-3-ethyl)indolylcarbonyl chloride (D11) (1 g) in dry dichloromethane (100 ml) was added dropwise a mixture of endo-3-amino-8-azabicyclo[3,2,1]octane (0.7 g) and triethylamine (0.7 ml) in dry dichloromethane (50 ml). The reaction mixture was stirred at room temperature overnight, the solvent was then evaporated in vacuo. The residue dissolved in 5N hydrochloric acid solution (20 ml) and washed with diethyl ether (50 ml). The aqueous phase was basified with potassium carbonate and then extracted with dichloromethane (3×75 ml). The organic phase was dried (Na$_2$SO$_4$), the solvent was evaporated in vacuo and the residue filtered through a short alumina column. The product was isolated as the hydrochloride salt (E14) (1.27 g, 76%) m.p. 263°–4°.

$^1$H-NMR (d$_6$-DMSO) 270 MHz: δ 10.80–10.20 (m, 1H), 7.80 (d, 1H), 7.25–7.05 (m, 2H), 6.95–6.80 (m, 1H), 6.32 (bs, 1H), 4.10 (t, 1H), 3.90–3.65 (m, 4H), 3.55–3.10 (m, 1H), 2.65 (bs, 3H), 2.60–2.00 (m, 8H), 1.90–1.65 (m, 1H), 1.60–1.40 (m, 1H), 0.92 (t, 3H).

EXAMPLE 15 endo-N-(8-Methyl-8-azabicyclo[3.2.1]-oct-3-yl)-3-ethylindole-1-carboxamide hydrochloride (E15)

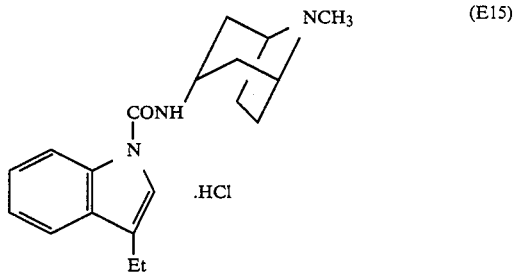

Following the procedure outlined in Example 6, reaction of endo-N-(8-methyl-8-azabicyclo[3.2.1]oct-3-yl)2,3-dihydro-3-ethylindole-1-carboxamide hydrochloride (E14) (1.01 g) with 2,3-dichloro-5,6-dicyano-1,4-benzoquinone (0.8 g) afforded the title compound (E15) (0.4 g, 40%) m.p. 210°–13°.

$^1$H-NMR (d$_6$-DMSO) 270 MHz: δ10.90–10.50 (m, 1H), 8.15 (d, 1H), 7.90 (bs, 1H), 7.68 (s, 1H), 7.55 (d, 1H), 7.35–7.10 (m, 2H), 4.10–3.65 (m, 3H), 2.90–2.05 (m, 13H), 1.30 (t, 3H).

EXAMPLE 16 endo-N-(8-Methyl-8-azabicyclo[3.2.1]oct-3-yl)-2,3-dihydro-5-nitroindole-1-carboxamide (E16)

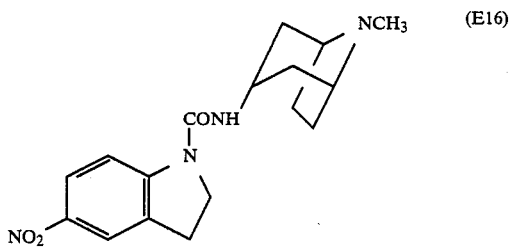

Following the procedure outlined in Example 1, reaction of 1-(2,3-dihydro-5-nitro)indolyl trichloromethyl carbamate (D12) (2 g) with endo-3-amino-8-azabicyclo[3.2.1]octane (0.9 g) afforded the title compound (E16) (1.25 g, 62%) m.p. 176°–8°.

$^1$H-NMR (CDCl$_3$) 270 MHz: 8.18–7.95 (m, 3H), 5.05 (bd, 1H), 4.15–3.95 (m, 3H), 3.35–3.15 (m, 4H), 2.30 (s, 3H), 2.35–2.10 (m, 4H), 1.85–1.60 (m, 4H).

EXAMPLE 17 endo-N-(8-Methyl-8-azabicyclo[3.2.1]oct-3-yl)-2,3-dihydro-6-nitroindole-1-carboxamide hydrochloride (E17)

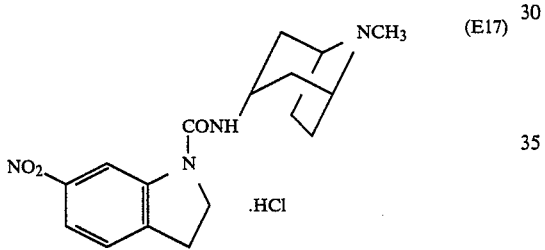

Following the procedure outlined in Example 1, reaction of 1-[1-(2,3-dihydro-6-nitro)indolylcarbonyl]imidazole (D13) (4.7 g) with endo-3-amino-8-methyl-8-azabicyclo[3.2.1]octane (2.55 g) afforded the title compound (E17) m.p. 245°–7° (decomposition).

$^1$H-NMR (d$_6$-DMSO) 270 MHz: δ10.15–9.95 (m, 1H), 8.55 (d, 1H), 7.85–7.70 (m, 1H), 7.45–7.35 (m, 1H), 6.65–6.55 (m, 1H), 4.15 (t, 2H), 3.90–3.70 (m, 1H), 3.60–3.35 (m, 2H), 3.30–3.15 (t, 2H), 2.65 (d, 3H), 2.45–2.00 (m, 8H).

EXAMPLE 18

N-(1-Azabicyclo[2.2.2]oct-3-yl)2,3-dihydro-3,3-dimethylindole-1-carboxamide hydrochloride (E18)

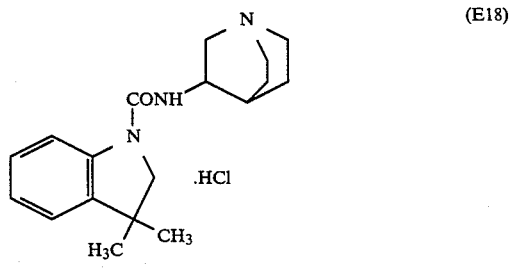

To a solution of 3-amino-1-azabicyclo[2.2.2]octane dihydrochloride (0.87 g) in water (1.5 ml) was added dry dimethylformamide (30 ml) and triethylamine (2 ml). The mixture was stirred at room temperature for 5 min, then a solution of 1-(2,3-dihydro-3,3-dimethyl)indolylcarbonyl chloride (D14) in dry dimethylformamide (20 ml) was added dropwise. The reaction mixture was stirred at room temperature for 18h, the solvent was then evaporated in vacuo. The residue was dissolved in 5N hydrochloric acid solution (25 ml) and washed with diethyl ether (50 ml). The aqueous phase was basified with potassium carbonate and then extracted with dichloromethane (3×75 ml). The organic phase was dried (Na$_2$SO$_4$), the solvent was evaporated in vacuo and the residue crystallised from ethyl acetate/diethyl ether to give the title compound (E18) m.p. 174°–6°.

$^1$H-NMR (CDCl$_3$) 270 MHz: 11.40 (bs, 1H), 7.95 (d, 1H), 7.25–7.05 (m, 2H), 6.95 (t, 1H), 6.65 (bd, 1H), 4.60–4.40 (m, 1H), 4.28 (dd, 1H), 4.10–3.80 (m, 3H), 3.55–3.35 (m, 1H), 3.30–3.00 (m, 3H), 2.50–2.30 (m, 2H), 2.25–1.90 (m, 1H), 1.95–1.60 (m, 2H), 1.35 (s, 6H).

EXAMPLE 19

(endo)-N-(8-Methyl-8-azabicyclo[3.2.1]oct-3-yl)-2,3-dihydro-2-methylindole-1-carboxamide hydrochloride (E19)

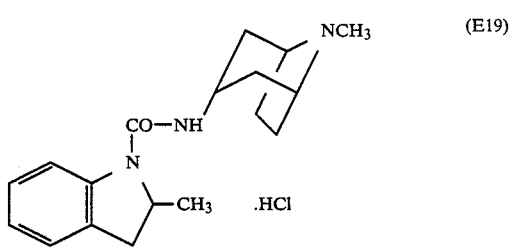

To 1-(2,3-dihydro-2-methyl)indolylcarbonyl chloride (D18) (0.5 g) in dry dichloromethane (50 ml) was added dropwise a mixture of (endo)-8-methyl-8-azabicyclo[3.2.1]octan-3-amine (0.36 g) and triethylamine (0.36 ml) in dry dichloromethane (25 ml). The reaction mixture was stirred at ambient temperature overnight, the solvent was then evaporated under reduced pressure. The residue was dissolved in 5N hydrochloric acid solution (20 ml) and was washed with diethyl ether (50 ml). The aqueous phase was basified with potassium carbonate and then the product was extracted into dichloromethane (3×50 ml). The organic phase was dried (Na$_2$SO$_4$), the solvent was evaporated under reduced pressure and the residue filtered through a short alumina column eluting with 25% dichloromethane/75% chloroform. The product was isolated as the hydrochloride salt from ethyl alcohol and diethyl ether to give the title compound (E19) (0.64 g, 78%) mp 292°–3° C.

$^1$H-NMR (d$_6$-DMSO) 270 MHz: δ10.38 (bs, 1H), 7.78 (d, 1H), 7.18 (d, 1H), 7.08 (t, 1H), 6.85 (t, 1H), 6.30 (bs, 1H), 4.85–4.70 (m, 1H), 3.90–3.65 (m, 3H), 3.32 (s, 3H), 2.85–2.00 (m, 10H), 1.15 (d, 3H).

EXAMPLE 20

(endo)-N-(8-Methyl-8-azabicyclo[3.2.1]oct-3-yl)-2,3-dihydro-2,3-dimethylindole-1-carboxamide (E20)

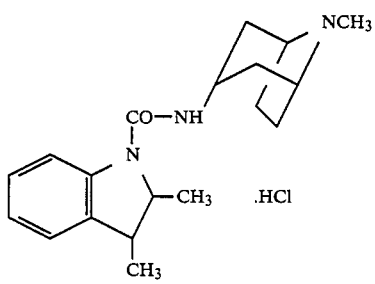

Following the procedure outlined in Example 19, reaction of 1-(2,3-dihydro-2,3-dimethyl)indolylcarbonyl chloride (D19) (0.58 g) with (endo)-8-methyl-8-azabicyclo[3.2.1]octan-3-amine (0.39 g) and triethylamine (0.39 ml) afforded, after crystallisation from ethyl acetate, the title compound (E20) (0.43 g, 35%). m.p. 134°–6°.

$^1$H-NMR (CDCl$_3$) 270 MHz: δ7.70–7.55 (m, 1H), 7.25–7.10 (m, 2H), 7.00–6.90 (m, 1H), 5.20–5.05 (m, 1H), 4.45–4.35 (m, 0.15H), 4.10 (q, 0.85H), 3.85 (dq, 0.85H), 3.65–3.50 (m, 0.15H), 3.25–3.10 (m, 2H), 2.90–2.75 (m, 1H), 2.30 (s, 3H), 2.40–2.05 (m, 4H), 1.90–1.60 (m, 4H), 1.40–1.10 (m, 6H).

EXAMPLE 21

(endo)-N-(8-Methyl-8-azabicyclo[3.2.1]oct-3-yl)-2,3-dihydro-2,3,3-trimethylindole-1-carboxamide hydrochloride (E21)

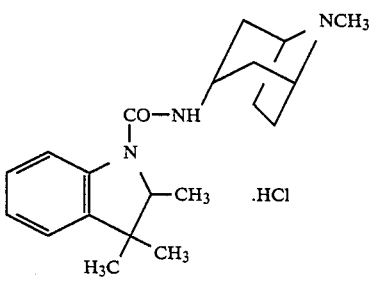

Following the procedure outlined in Example 19, reaction of 1-(2,3-dihydro-2,3,3-trimethyl)indolylcarbonyl chloride (D20) (0.6 g) with (endo)-8-methyl-8-azabicyclo[3.2.1]octan-3-amine (0.38 g) and triethylamine (0.37 ml) afforded, after addition of ethanolic-hydrochloride, the title compound (E21) (0.5 g, 51%) m.p. 225°–6°.

$^1$H-NMR (d$_6$-DMSO) 270 MHz: 10.50 (bs, 1H), 7.75 (d, 1H), 7.20–7.05 (m, 2H), 6.90 (t, 1H), 6.35 (bs, 1H), 4.45–4.30 (m, 1H), 3.90–3.70 (m, 3H), 2.90–2.05 (m, 8H), 2.65 (bs, 3H), 1.25 (s, 3H), 1.15 (s, 3H), 1.05 (d, 3H).

EXAMPLE 22

(endo)-N-(8-Methyl-8-azabicyclo[3.2.1]oct-3-yl)-2,3-dihydro-3-isopropylindole-1-carboxamide hydrochloride (E22)

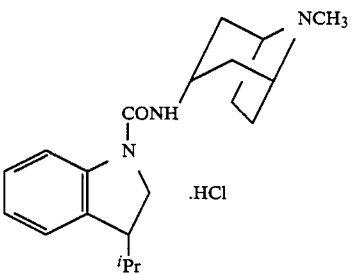

Following the procedure outlined in Example 14, reaction of 1-(2,3-dihydro-3-isopropyl)indolylcarbonyl chloride (D21) (0.5 g) with (endo)-8-methyl-8-azabicyclo[3.2.1]octan-3-amine (0.31 g) and triethylamine (0.31 ml) afforded, after addition of ethanolic-hydrochloride, the title compound (E22) (0.7 g, 86%) m.p. 278°–80° dec. $^1$H-NMR (d$_6$-DMSO) 400 MHz: 10.52 (bs, 1H), 7.80 (d, 1H), 7.15 (d, 1H), 7.10 (t, 1H), 6.85 (t, 1H), 6.40 (bs, 1H), 4.00–3.85 (m, 2H), 3.85–3.65 (m, 3H), 2.65 (s, 3H), 2.85–1.90 (m, 10H), 0.95 (d, 3H), 0.70 (d, 3H).

EXAMPLE 23

(endo)-N-(8-Methyl-8-azabicyclo[3.2.1]oct-3-yl)-2,3,4,4a,9,9a-hexahydrocarbazole-1-carboxamide (E23)

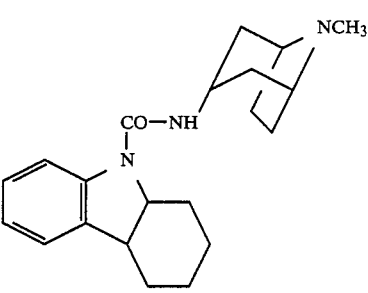

Following the procedure outlined in Example 19, reaction of 1-(2,3,4,4a,9,9a-hexahydro)carbazolylcarbonyl chloride (D22) (0.44 g) with (endo)-8-methyl-8-azabicyclo[3.2.1]octan-3-amine (0.15 g) and triethylamine (0.15 ml) afforded, after crystallisation from ethyl acetate, the title compound (E23) (0.19 g, 53%) m.p. 155°–6°.

$^1$H-Nmr (CDCl$_3$) 400 Mhz: δ7.58 (d, 1H), 7.22–7.10 (m, 2H), 6.98 (t, 1H), 5.12 (bd, 1H), 4.25–4.04 (m, 2H), 3.52–3.42 (m, 1H), 3.28–3.16 (m, 2H), 2.42–2.10 (m, 5H), 2.34 (s, 3H), 2.08–1.96 (m, 1H), 1.96–1.50 (m, 7H), 1.32–1.12 (m, 3H).

Pharmacology

Antagonism of the von Bezold-Jarisch reflex

The compounds were evaluated for antagonism of the von Bezold-Jarisch reflex evoked by 5-HT in the anaesthetised rat according to the following method:

Male rats, 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5HT-evoked response to 50% of the control response ($ED_{50}$) was then determined.

The results were as shown in Table 1.

TABLE 1

| Compound of Example No. | $ED_{50}$ μg/kg i.v |
|---|---|
| 1 | 12.5 |
| 2 | 1.4 |
| 3 | 5 |
| 4 | 3 |
| 5 | 0.58 |
| 6 | 1.6 |
| 7 | >10 |
| 8 | 17 |
| 9 | >10 |
| 10 | 7 |
| 11 | 7.7 |
| 12 | 4.4 |
| 13 | 3.9 |
| 14 | 1.0 |
| 15 | 2.0 |
| 16 | >10 |
| 17 | >10 |
| 18 | 5.3 |
| 19 | 0.79 |
| 20 | 0.53 |
| 21 | 1.4 |
| 22 | 0.56 |

We claim:

1. A compound of formula (I), or a pharmaceutically acceptable salt thereof:

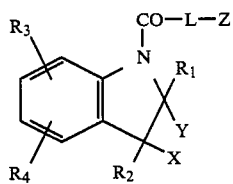

(I)

wherein
L is NH;
X and Y are independently selected from hydrogen or $C_{1-4}$ alkyl;
$R_1$ and $R_2$ are independently selected from hydrogen, $C_{1-6}$ alkyl, $C_{2-6}$ alkenyl-$C_{1-4}$ alkyl, or together are $C_{2-4}$ polymethylene;
$R_3$ and $R_4$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro, amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;
Z is a group of formula (a),

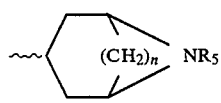

(a)

wherein n is 2 or 3; and $R_5$ is $C_{1-7}$ alkyl, $C_{3-8}$ cycloalkyl, $C_{3-8}$ cycloalkyl-$C_{1-2}$ alkyl or $C_{2-7}$ alkenyl-$C_{1-4}$ alkyl.

2. A compound according to claim 1 of formula (II):

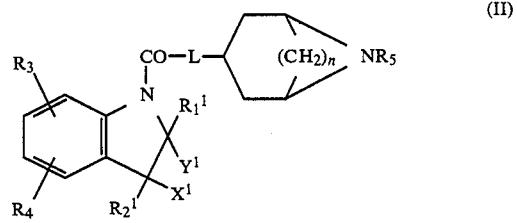

(II)

wherein $X^1$ and $Y^1$ are independently selected from hydrogen, methyl or ethyl, $R_1^1$ and $R_2^1$ are independently hydrogen, methyl or ethyl and the remaining variables are as defined in claim 1.

3. A compound according to claim 2 wherein n is 2.

4. A compound according to claim 3 wherein $R_5$ is methyl.

5. A compound according to claim 1 wherein one of $R_3$ and $R_4$ is hydrogen and the other is selected from hydrogen, 5-chloro and 5-fluoro.

6. endo-N-(8-Methyl-8-azabicyclo[3.2.1]oct-3-yl)-2,3-dihydro-3,3-dimethylindole-1-carboxamide hydrochloride.

7. A pharmaceutical composition for use in the treatment of anxiety or psychosis comprising an effective amount of a compound according to claim 1, and a pharmaceutically acceptable carrier.

8. A method of treatment of anxiety or psychosis in mammals, which comprises the administration to the mammal in need of such treatment, an effective amount of a compound according to claim 1.

9. A compound selected from the group consisting of:
endo-N-(9-methyl-9-azabicyclo[3.3.1]non-3-yl)-2,3-dihydroindole-1-carboxamide,
endo-N-(8-methyl-8-azabicyclo[3.2.1]oct-3-yl)-2,3-dihydroindole-1-carboxamide,
endo-N-(8-methyl-8-azabicyclo[3.2.1]oct-2,3-dihydro-3-methylindole-1-carboxamide,
endo-N-(8-methyl-8-azabicyclo[3.2.1]oct-3-yl)-2,3-dihydro-3,3-dimethylindole-1-carboxamide,
endo-N-(8-ethyl-8-azabicyclo[3.2.1]-oct-3-yl)-2,3-dihydroindole-1-carboxamide,
endo-N-(8-methyl-8-azabicyclo[3.2.1]oct-3-yl)-5-fluoro-2,3-dihydroindole-1-carboxamide,
endo-N-(8-methyl-8-azabicyclo[3.2.1]oct-3-yl)-2,3-dihydro-5-chloroindole-1-carboxamide,
endo-N-(8-methyl-8-azabicyclo[3.2.1]oct-3-yl)-2,3-dihydro-5-methoxyindole-1-carboxamide,
endo-N-(8-methyl-8-azabicyclo[3.2.1]oct-3-yl)-2,3-dihydro-3-ethylindole-1-carboxamide,
endo-N-(8-methyl-8-azabicyclo[3.2.1]oct-3-yl)-2,3-dihydro-5-nitroindole-1-carboxamide,
endo-N-(8-methyl-8-azabicyclo[3.2.1]oct-3-yl)-2,3-dihydro-6-nitroindole-1-carboxamide,
or pharmaceutically acceptable salts of any of the foregoing.

10. A method of treatment of migraine and cluster headache in mammals, which comprises the administration to the mammal in need of such treatment, an effective amount of a compound according to claim 1.

11. A method of treatment of trigeminal neuralgia in mammals, which comprises the administration to the mammal in need of such treatment, an effective amount of a compound according to claim 1.

12. A method of treatment of emesis in mammals, which comprises the administration to the mammal in need of such treatment, an effective amount of a compound according to claim 1.

* * * * *

UNITED STATES PATENT AND TRADEMARK OFFICE
CERTIFICATE OF CORRECTION

PATENT NO. : 4,871,744

DATED : October 3, 1989

INVENTOR(S) : Francis D. King and Karen A. Joiner

It is certified that error appears in the above-identified patent and that said Letters Patent is hereby corrected as shown below:

Claim 6, column 30, lines 24-25, "hydrochloride" should be -- or a hydrochloride salt thereof --;

Claim 7, column 30, lines 26-27, "for use in the treatment of anxiety or psychosis" should be deleted;

Claim 9, column 30, line 38, "oct-2,3" should be -- oct-3-yl)-2,3 --;

Claim 9, column 30, line 42, "[3.2.1]-oct" should be -- [3.2.1]oct --.

Signed and Sealed this

Eighteenth Day of December, 1990

Attest:

HARRY F. MANBECK, JR.

*Attesting Officer*  *Commissioner of Patents and Trademarks*